US00PP33157P3

(12) United States Plant Patent
Shipley

(10) Patent No.: US PP33,157 P3
(45) Date of Patent: Jun. 15, 2021

(54) TURPENTINE PLANT NAMED 'BUTTERBLOOM'

(50) Latin Name: *Ericameria laricifolia*
Varietal Denomination: Butterbloom

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 73 days.

(21) Appl. No.: 16/350,154

(22) Filed: Oct. 9, 2018

(65) Prior Publication Data

US 2020/0113097 P1 Apr. 9, 2020

(51) Int. Cl.
*A01H 5/00* (2018.01)
*A01H 6/14* (2018.01)
*A01H 6/36* (2018.01)

(52) U.S. Cl.
USPC ..... Plt./226
CPC ..... *A01H 6/14* (2018.05); *A01H 6/36* (2018.05)

(58) Field of Classification Search
USPC ..... Plt./226
CPC ..... A01H 5/02; A01H 5/00
See application file for complete search history.

*Primary Examiner* — Kent L Bell

(57) ABSTRACT

A new and distinct *Ericameria laricifolia* plant named 'Butterbloom' is characterized by compact habit, even growth and excellent tolerance to pruning.

3 Drawing Sheets

Latin name: *Ericameria laricifolia.*
Varietal denomination: 'Butterbloom'.

BACKGROUND OF THE INVENTION

Turpentine bush, *Ericameria laricifolia* is an evergreen, much branched, bright green shrub with soft, needle like resinous leaves native to much of southwestern North America between the elevations of about 2500-6000 feet. *Ericameria laricifolia* is a member of the *Ericameria* section of the genus *Ericameria* which is a member of the Astereae tribe of the sunflower family, Asteraceae. *Ericameria laricifolia* can be found in the states of California, Nevada, Utah, Arizona, New Mexico, and Texas in the U.S. and in the states of Sonora and Chihuahua, Mexico.

Turpentine bush illuminates the hillsides and mountains of the Southwest with its bright yellow flowers from August-November, although some flowers can be produced nearly year round under favorable conditions. Plants in the wild vary in size from as small as 1×1 foot (height×width) to as large as 4×6 feet depending upon site growth conditions and population variation.

Turpentine bush is a popular landscape plant in the southwestern U.S. finding uses as a foundation plant, low informal or clipped hedge, seasonal color plant as well as a specimen shrub. In cultivation most cultivars will reach the larger maximum size listed above without pruning. *Ericameria laricifolia* generally tolerates pruning well and is long lived in the landscape.

The present invention relates to a new and distinct cultivar of *Ericameria laricifolia*. The new cultivar originated as a single plant grown from seeds collected from a nursery population of unnamed open pollinated *Ericameria* plants in 2008 near Tucson, Ariz. and is the object of this application. The new plant is notable by its unique dense and even growth form, distinguishable from its possible female parent. The male parent is unknown. The nursery population which contained both parents is highly variable in growth form but generally more open and less dense than 'Butterbloom'. Most available turpentine bushes are seed grown from open pollinated source plants and are generally relatively open in growth form.

SUMMARY OF THE INVENTION

Among the features that distinguish the new turpentine bush cultivar from all other available and commercial varieties of turpentine bush known to the inventor are the following combination of characteristics: plants of even and compact growth form, as if hedged as well as very tolerant of pruning. Irrigated plants at 4 years of age are about 3 feet tall by 5 feet wide.

The propagation procedure is as follows: Cuttings are taken from long sprouts with growth less than one year old. These sprouts are cut into 3 inch long cuttings, then placed in DIP'N GRO™ solution (20 parts water to 1 part DIP'N GRO™) for 15 seconds, then planted into a tray filled with a 50% peat/50% perlite mix. Trays are placed into a rooting greenhouse maintained between 70-85° F. and relative humidity between 85-93% under mist watering. Bottom heat is applied as needed during the cool season only. Rooting is generally completed within 3½ weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Ericameria laricifolia* 'Butterbloom' growing near Tucson, Ariz., depicted in color as nearly correct as it is possible to make in a color illustration of the character.

DETAILED PLANT DESCRIPTION

Figure 1:
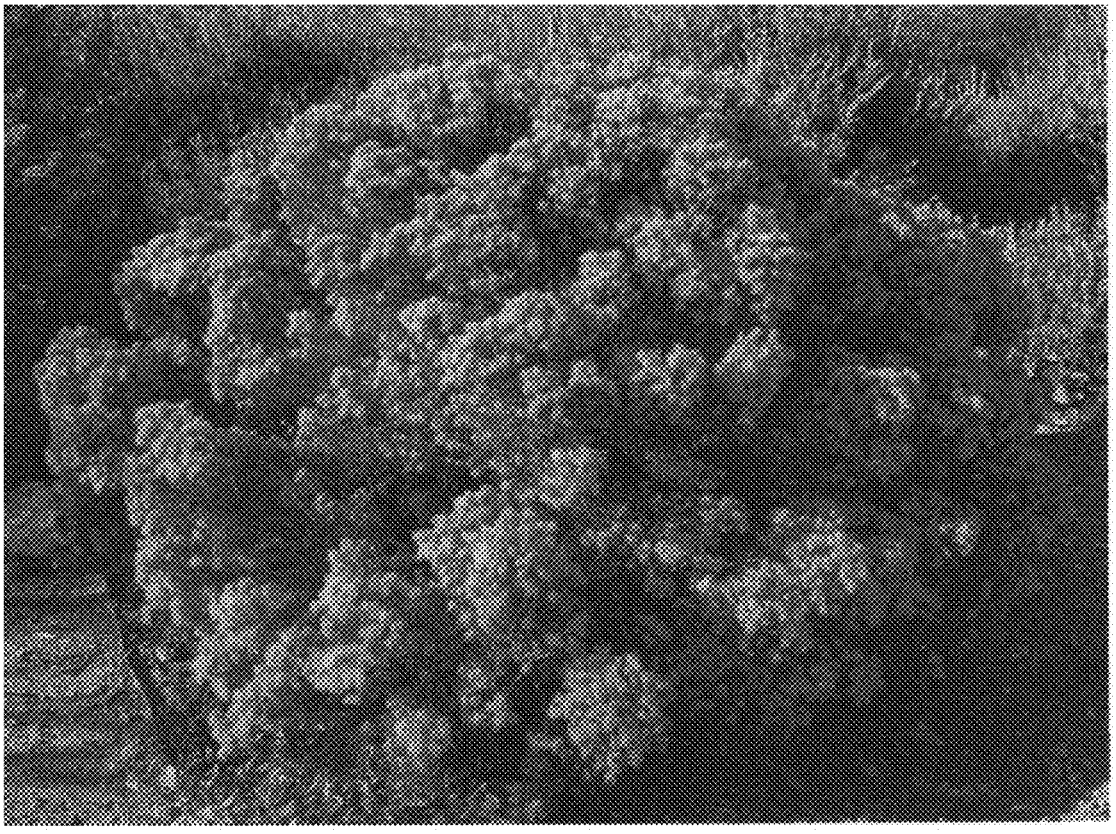
FIG. 1 shows *Ericameria laricifolia* 'Butterbloom' at age 3 in bloom near Tucson, Ariz.
Figure 2:
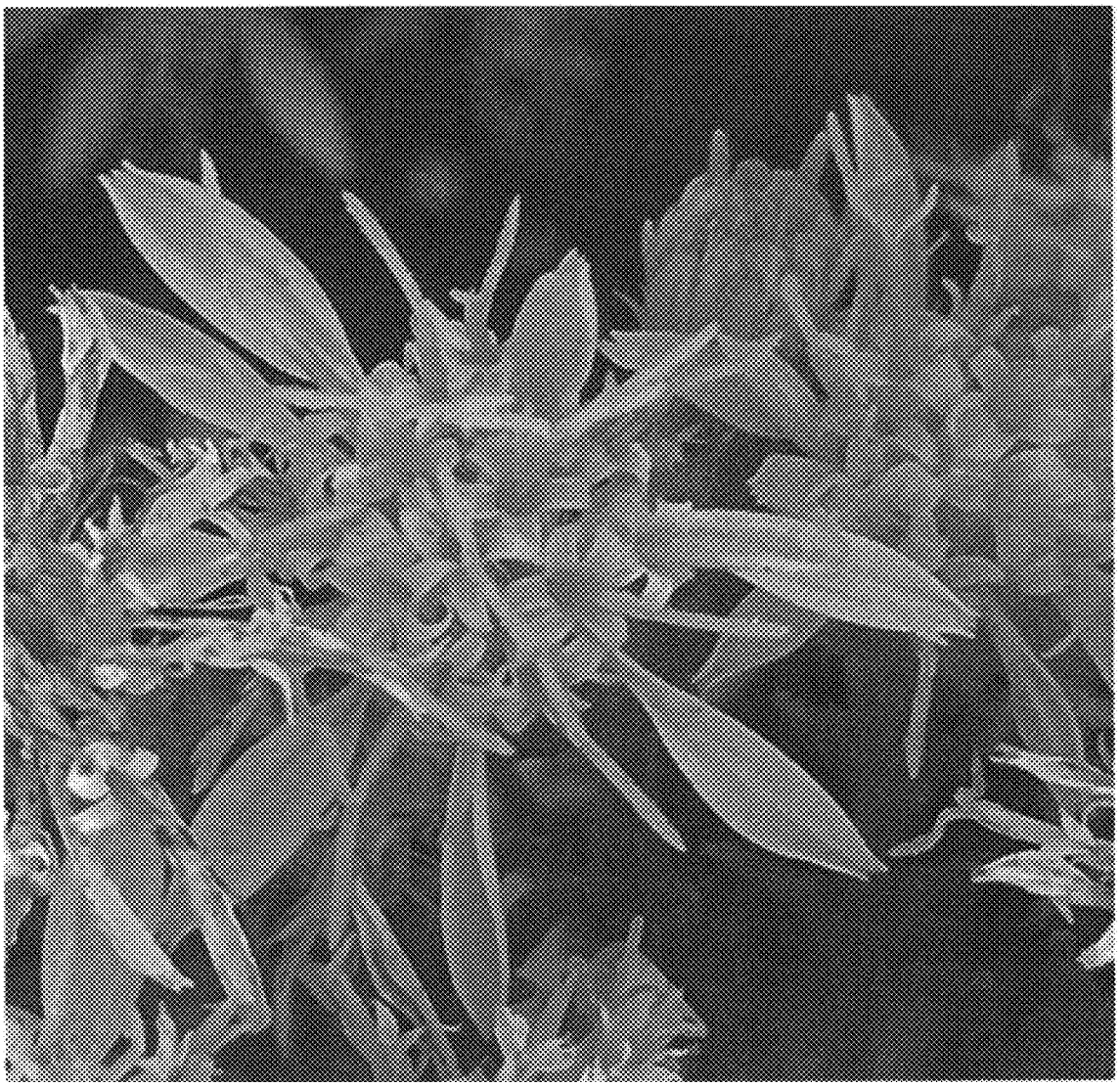
FIG. 2 shows *Ericameria laricifolia* 'Butterbloom' flowering heads at various stages of development.
Figure 3:
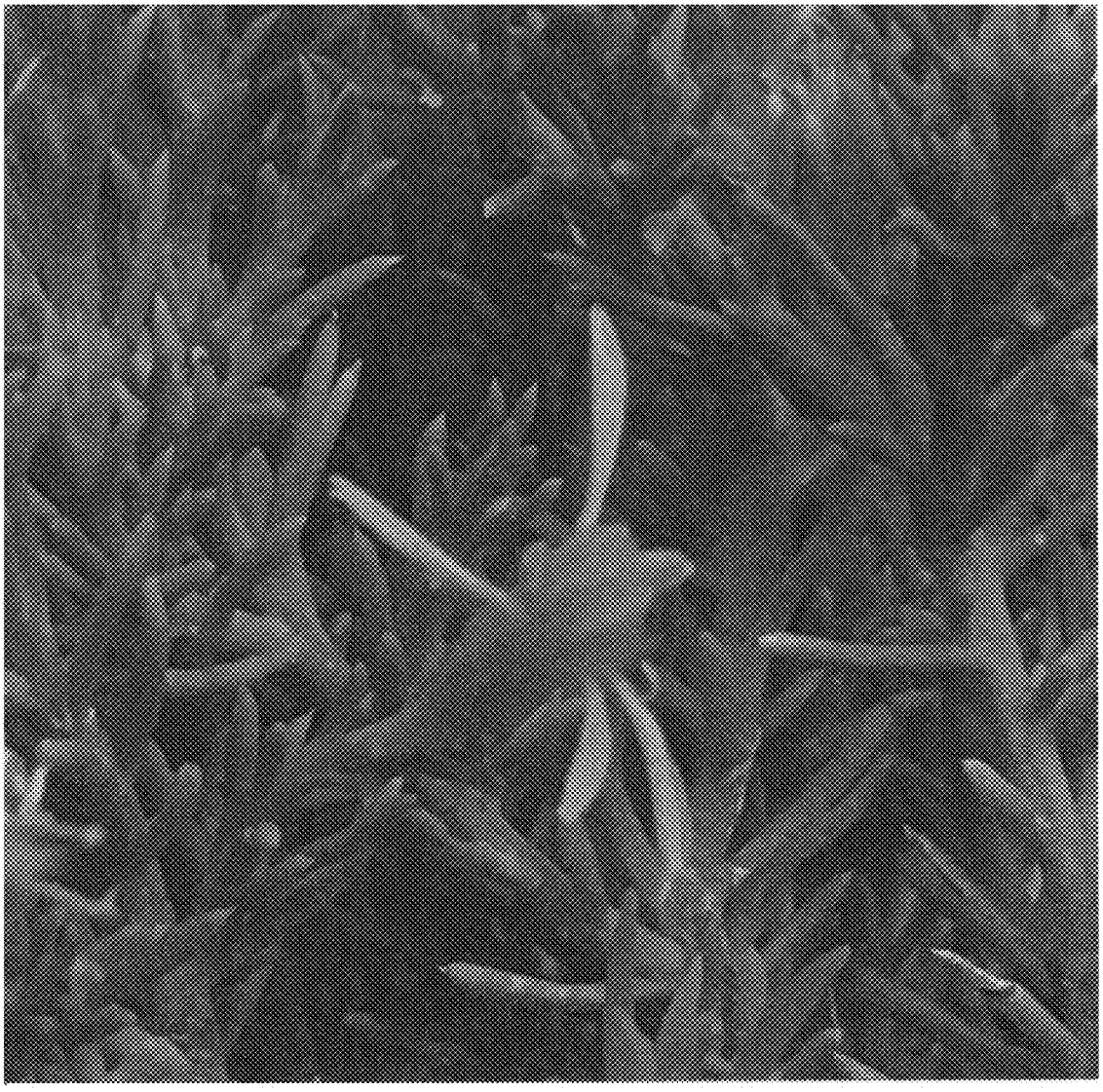
FIG. 3 shows *Ericameria laricifolia* 'Butterbloom' leaves, stems and an inflorescence in early bloom

The following is a detailed description of the new turpentine bush plant based upon potted plants at about age 1 year and a more mature specimen growing near Tucson, Ariz. aged 4 years.

The color descriptions are based upon the 5$^{th}$ edition R.H.S. Colour Chart. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

Plant a much branched evergreen shrub, reaching 3 feet tall×5 feet tall by age 4 years.

Leaves: Alternate, glabrous, resinous, containing numerous tiny glands (0.1 mm diameter, color closest to 141B), leaves highly variable in size and profile, shade leaves being quite flattened, while leaves grown in full sun appear needle like. Shade leaves 1.5-2 mm wide×11-24 mm long with a barely visible midrib, veins not visible. Shade leaves linear, apiculate, acute at the base, the leaf flattened, entire, resinous, color of both adaxial and abaxial surfaces 141B. Sun leaves 1-1.25 mm wide×10-12 mm, approaching terete in profile except for some adaxial flattening. Midrib not visible. Leaves resinous, linear, apiculate, entire and acute at the base. Color of both adaxial and abaxial surfaces closest to 141B. Stipules absent. Axillary buds obscure.

Stems: Highly branched, young stems similar to the leaves in color (141C), resinous surface and glands. Young stems faintly striate. Internode length 2-7 mm, stem diameter 0.75-1.5 mm. As stems mature the color grades to 164C at 2 mm diameter and 199D at 5 mm or more. At about 3 mm diameter the bark begins to shred longitudinally. This process continues as the stems thicken. By the time the stems reach 2-3 inches in diameter the bark becomes mottled and longitudinally furrowed and rough to the touch. Color grades from 164D to 201B on older bark. Flowers arranged in terminal heads, the heads measuring about 18 mm in depth×18-20 mm wide including the florets. Involucre comprised of graduated phyllaries. Involucre measures 5-7 mm long×3-4 mm in diameter, more or less campanulate in shape.

Phyllaries: Somewhat spreading at the tips, glabrous, entire, apiculate, lanceolate. Each phyllary with a pair of glands abaxially at the base, these more or less spherical, 0.5 mm diameter, gland color 143B. Basal phyllaries 3 mm long×1 mm wide; apical phyllaries 5 mm long×1.5 mm wide. The longitudinal central ¼ portion of the phyllaries is colored 145A, which grades to scarious margins colored 150D. The tips of the apical phyllaries are colored 165A, while the tips of the basal phyllaries is colored as the central portion (145A). Adaxially the phyllaries are similar to and colored like the abaxial surface except the glands are only present on the abaxial side.

Ray florets: Numbering 6-8, typically 7, pistillate, lacking stamens. Ovary inferior, measuring 2-3 mm long×1 mm wide, colored 154A, oblanceoloid in shape, somewhat flattened dorsally, the surface sericeous. Floret corolla fused into a tube with a strap shaped radial extension. Ray floret corolla tube 3 mm long×0.5 mm diameter. Ray floret corolla strap 7 mm long×2 mm wide, elliptical-oblanceolate in shape with 2-3 fine teeth at the apex, otherwise the strap margin is entire. Strap base is acute. Ray floret corolla color 2A. Pappus comprised of about 15 capillary bristles attached at the apex of the ovary, 4-6 mm long. Stigma exserted, 2 lobed, the recurved lobes colored 2A. Stigma lobes measure 2.5 mm long×0.2 mm diameter. Style about 6-7 mm long×0.25 mm diameter, colored like the floret corolla. Unopened ray floret mature buds oblanceoloid, 7 mm long×1 mm diameter (8 mm long including ovary) colored 2A at the apex grading to 1C near the base.

Disc florets: Numbering 7-11 per head, perfect, protandrous. Disc floret corolla with 5 petals fused into a flaring tube with 5 acute radial petal lobes, these recurved and glabrous, the lobes measuring 2 mm long×1 mm wide. Disc floret corolla glabrous except for scattered short hairs below the corolla lobes. Disc floret corolla translucent, color closest to 1C. Tube colored as disc floret corolla lobes. Disc floret corolla measures 6-7 mm long. Stamens 5, united into a tube around the style, inserted in the corolla. Disc floret stamens mature more or less at the time of ray floret opening but before the stigmas of the disc florets have matured. Stamens at maturity are colored 13A, gradually changing to 22A as they age. Dry anthers measure 3 mm long×0.5 mm diameter. Pollen color 13A, released 1-2 days prior to petal spreading. Pappus comprised of numerous capillary bristles (about 20) from 5-7 mm long, the pappus attached near the apex of the ovary. Disc floret ovary measures about 3 mm long×1 mm wide, oblanceoloid, sericeous, color close to 154A. Disc floret style+stigma length 10 mm long, 0.2-0.25 mm diameter. Style colored 1C. Stigma 2 lobed, each about 2-3 mm long, colored 18A, spreading, from slightly ascending to slightly descending. The terminal portion of the stigma lobes is covered with fine, spreading hairs. Unopened mature disc floret buds oblanceoloid, 11 mm long to top of ovary, 1 mm in diameter, color 13C.

Fruit: An achene 3.5-4 mm long, 0.7 5mm thick at the widest point, dorsally compressed, angular, sericeous. Wind dispersed by the still attached pappus, the longest bristles 6 mm long. Achene color closest to 191B. Attachment point of achene colored closest to 155C. Distal tip of achene colored 163C at the floral scar.

COMPARISONS TO RELATED TURPENTINE BUSHES

The inventor knows no other patented *Ericameria laricifolia* cultivars. Two existing unpatented cultivars have been available in the nursery trade. 'Desert Mountain' is a seed based cultivar from a wild population in North Scottsdale. The plants are quite variable as this is an open pollinated population of plants. 'Desert Mountain' has been widely used for revegetation in the Phoenix area. In general, these plants have a feathery form growing to 2-3 feet tall×2-3 feet wide. This cultivar seems to have gone out of production, as the original grower no longer lists it either on its availability or grow lists. Cultivar 'Aguirre' is a clonal selection from New Mexico selected for showy flowers and rich green foliage. This cultivar is listed as growing to 2-3 feet tall and wide. A third cultivar called 'Texas Canyon' can be found listed on internet information sites, but no nurseries can be found that produce or sell it.

Compared to 'Desert Mountain', *Ericameria* 'Butterbloom' is more uniform, dense and even in growth habit. Bushes of 'Butterbloom' are rounded, compared to the feathery form of 'Desert Mountain'.

Compared to 'Aguirre', 'Butterbloom' is more uniform, dense and less open in growth form. Compared to the other cultivar descriptions, 'Butterbloom' is larger and less tall than wide at 3 feet tall×5 feet wide in the 4 year old individual examined. It should be noted that the phenotype of this species is quite plastic in response to both light and available water, such that the existing cultivars might reach sizes similar to 'Butterbloom' under favorable conditions.

I claim:

1. A new and distinct *Ericameria laricifolia* plant substantially as described and illustrated herein.

* * * * *